United States Patent [19]

Brake

[11] Patent Number: 5,091,584

[45] Date of Patent: Feb. 25, 1992

[54] PROCESS OF PREPARING FORMALDEHYDE/AMINE ADDUCTS

[75] Inventor: Loren D. Brake, Wilmington, Del.

[73] Assignee: E. I. Du Pont de Nemours and Company, Wilmington, Del.

[21] Appl. No.: 631,267

[22] Filed: Dec. 20, 1990

Related U.S. Application Data

[62] Division of Ser. No. 316,809, Feb. 28, 1989, Pat. No. 5,030,762.

[51] Int. Cl.$^5$ ............................................. C07C 209/24
[52] U.S. Cl. ................................................... 564/471
[58] Field of Search ................................ 564/508, 471

[56] References Cited

U.S. PATENT DOCUMENTS

| | | | |
|---|---|---|---|
| 2,101,215 | 12/1937 | Graves et al. | 564/503 X |
| 2,179,215 | 11/1939 | Jacobson | 564/471 |
| 2,287,464 | 6/1942 | Bock | 564/471 |
| 3,539,535 | 11/1970 | Wisner | 260/72 |
| 3,979,348 | 9/1976 | Ballweber et al. | 260/29.4 |
| 4,010,131 | 3/1977 | Phillips et al. | 260/29.4 |
| 4,026,807 | 5/1977 | Quinlan et al. | 564/471 X |
| 4,049,606 | 9/1977 | Hunter et al. | 260/29.4 |
| 4,179,424 | 12/1979 | Phillips et al. | 260/99.4 |
| 4,230,608 | 10/1980 | Mura | 260/29.4 |
| 4,390,659 | 6/1983 | Stanley, Jr. et al. | 524/555 |
| 4,395,311 | 7/1983 | McDonald | 564/503 X |
| 4,605,772 | 8/1986 | Darby et al. | 564/503 |

OTHER PUBLICATIONS

Walker, *Formaldehyde*, American Chemical Society Monograph Series, 3rd ed., pp. 360–361.

*Primary Examiner*—Richard L. Raymond

[57] ABSTRACT

A formaldehyde/amine adduct useful in water treatment having improved stability made by reacting formaldehyde and a secondary amine, limiting the water content of the adduct to no more than 30 weight percent, optionally, adding an alcohol.

11 Claims, No Drawings

PROCESS OF PREPARING FORMALDEHYDE/AMINE ADDUCTS

This is a division of application Ser. No. 07/316,809, filed Feb. 28, 1989, now U.S. Pat. No. 5,030,762.

FIELD OF INVENTION

This invention relates to a formaldehyde/amine adduct having improved stability made by reacting a formaldehyde and a secondary amine, limiting the water content of the adduct and, optionally, adding a $C_{1-3}$ alkyl alcohol.

BACKGROUND OF THE INVENTION

Water-soluble polymeric substances have found great utility in industry for applications such as sludge dewatering. They are used to flocculate dispersed particulate solids from aqueous suspensions, including sewage and effluents from industrial, mining and paper manufacturing operations.

Cationic and cationic quaternary ammonium polymers having excellent performance in sludge dewatering are delivered preformed or are made on-site. Neutral polymer is reacted with formaldehyde and a secondary amine or with a premix of formaldehyde and a secondary amine to form a cationic polymer and optionally followed by reaction with a quaternizing agent such as dimethylsulfate or methyl chloride to form cationic quaternary ammonium polymers When a premix is used, it is made shortly prior to reaction with the neutral polymer.

U.S. Pat. No. 3,979,348 teaches preparing an aqueous solution of a formaldehyde/secondary amine adduct, preferably in as concentrated a form as possible so as to minimize dilution effects on the end product. It teaches that, due to the concentrations of commercial aqueous solutions of formaldehyde and of aqueous amines, the concentration of the adduct is between 0.1 to 55 weight percent (wt.%).

U.S. Pat. No. 4,010,131 teaches reacting an aldehyde and a secondary amine to make an aldehyde/amine adduct in a 0.1 to 55 wt.% aqueous solution. The adduct is reacted with the polymer in a water-in-oil emulsion system followed by quaternization of the polymer using an alkylating agent.

U.S. Pat. No. 4,230,608 also teaches the reaction of a water-soluble polymer such as polyacrylamide with a formaldehyde/secondary amine premix followed by quaternization with an alkylating agent such as dimethylsulfate or methyl chloride. In each exemplification, the premix was reacted with the polymer shortly after being made.

U.S. Pat. No. 4,390,659 teaches a method for preparing these same quaternary polymeric complexes by simultaneously contacting a water soluble polymer with a lower aldehyde such as formaldehyde and a secondary amine such as dimethylamine, or the reaction product thereof, and a quaternizing agent. "Simultaneously contacting" means that the polymer, amine, aldehyde and at least a portion of the quaternizing agent are contacted prior to the substantial reaction of the polymer with the amine, aldehyde or their reaction product.

U.S. Pat. No. 4,049,606 teaches cationically modified polymers of acrylamide prepared by adding an aqueous solution of formaldehyde followed by adding a lower alkyl secondary amine.

U.S. Pat. No. 3,539,535 teaches a process for producing water-soluble, cationic carbamoyl polymers in the form of particulate solids by reacting carbamoyl polymers with formaldehyde and water-soluble, mono-functional, secondary amines. The formaldehyde and the amine are added simultaneously or as a premix.

U.S. Pat. No. 4,179,424 teaches adding formaldehyde and secondary amine to an acrylamide polymer. Paraformaldehyde dissolved in water is taught as a substitute for the 10 to 50 wt.% aqueous formaldehyde. In the Mannich Reaction Experiment, the formaldehyde and the amine were premixed if the reactor temperature was 100° C. and added in less than 15 seconds. Otherwise, the formaldehyde and the amine were simultaneously added to the polymer.

On-site preparation of formaldehyde-secondary amine adduct premix has several limitations.

For example, the amine and aldehyde must be shipped and stored by the user with the attendant added cost and risk of exposure to toxic chemicals. Both the aqueous aldehyde and the anhydrous or aqueous dimethylamine typically used in water treatment require special handling and storage considerations in that they have objectionable odor, are toxic and, in the case of the aqueous compounds, contain water that increases freight costs and the amount of storage needed. In the case of the anhydrous dimethylamine, pressure vessels are needed for shipping and storage.

A less odoriferous, more stable material that could be shipped and stored in non-pressure vessels and that could be added to a solution of the water-soluble polymer on-site to make a Mannich modified polymer that can be quaternized and is effective for dewatering sludges would be desirable.

Applicant has found that by limiting the water content of the adduct to 30 wt.% or less that an adduct of improved stability results. Also, he has found that further improvements, particularly when storage is at higher temperatures, can be achieved through the addition of a straight chain $C_{1-3}$ alkyl alcohol. In the absence of added alcohol, lower temperatures improve stability. Thus, the adduct premix need not by made just prior to use. A premix can be made and shipped to the place of use. The user then needs only one storage facility for the adduct instead of one for the formaldehyde and one for the amine. Because the product contains less water, shipping, handling and storage costs are reduced.

SUMMARY OF THE INVENTION

The present invention comprises a stable formaldehyde/amine adduct of the form $R^1R^2N\text{-}CH_2OR^3$, wherein $R^1$ and $R^2$ are straight chain alkyl groups containing from one to three carbons and $R^3$ is alternatively hydrogen or a straight chain alkyl group containing from one to three carbons. Preferably, $R^1$ and $R^2$ are methyl groups and $R^3$ is hydrogen or a methyl group. The adduct is formed and stored in the presence of up to 30 wt.% water, preferably less than 2 wt.% water, more preferably in the absence of water. Most preferably, the adduct with or without water being present, is formed and stored in the presence of up to two moles of a straight chain $C_{1-3}$ alkyl alcohol, preferably methyl alcohol, per mole of formaldehyde.

Storage of the adduct at lower temperatures improves the shelf life of the formaldehyde/amine adduct. Temperatures as low as 0° C. can be employed. While lower temperatures may be used, there is an economic penalty associated with decreasing temperatures. Adducts containing water are stored at 0° to 30° C., preferably 0° to 15° C., and most preferably at 0° to 5° C.

The adduct formed is less odoriferous than the components used in making it and has improved stability.

This stable adduct can be reacted with a water-soluble polymer such as polyacrylamide to prepare a Mannich modified polymer which is effective alone or in its quaternized form in dewatering sludges. The Mannich-modified polymer that results has the following form:

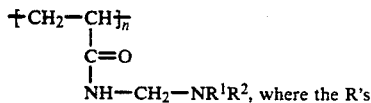

are as defined above and n is any number that results in a satisfactory molecular weight. This Mannich modified polymer may be quaternerized with any known quaterizing agent such as dimethylsulfate or methyl chloride.

The product of this invention may have additional uses in industries other than water treatment. For instance, by quaternizing the adduct, a product useful in industries requiring the absorption of sulfur compounds produced by the combustion of sulfur-containing hydrocarbon materials may be formed. See U.S. Pat. No. 4,605,772.

It has been found that this stable formaldehyde/amine adduct can be made by reacting secondary straight-chain alkyl amines having from 1 to 3 carbon atoms or a mixture of such amines, preferably dimethylamine, with formaldehyde in a one-step or a two-step process.

In the two-step reaction, the first step comprises reaction of about two moles of dialkylamine per one mole of formaldehyde to form an alkylene bis(dialkylamine) which is isolated from a water phase. The second step is the reaction of about one mole of alkylene bis(dialkylamine) per mole of formaldehyde or paraformaldehyde.

In summary, the preferred formaldehyde/amine adduct, $(CH_3)_2N\text{-}CH_2\text{-}OR^3$ where $R^3$ is hydrogen or a methyl group, in the presence of less than 30 wt.% water, can be prepared by:

(1) the addition of anhydrous dimethylamine to 57% aqueous formaldehyde, (2) the addition of anhydrous dimethylamine to a suspension of paraformaldehyde in an inert solvent such as methanol, (3) the addition of paraformaldehyde to bis(dimethylamino)methane [made by first reacting two moles of dimethylamine with one mole of formaldehyde and than separating the resulting bis(dimethylamine)methane from the water], (4) the addition of paraformaldehyde to bis(dimethylamino)methane in methanol, (5) the addition of 57% aqueous formaldehyde to bis(dimethylamino)methane, (6) the addition of anhydrous dimethylamine to a mixture of paraformaldehyde and aqueous formaldehyde, and (7) the reaction of aqueous dimethylamine with paraformaldehyde, aqueous formaldehyde or a mixture of the two.

(8) the addition of an alcohol such as methanol to the product of (1) above.

DETAILED DESCRIPTION OF INVENTION

Composition

The present invention comprises a stable formaldehyde/amine adduct of the form $R^1R^2N\text{-}CH_2OR^3$, wherein $R^1$ and $R^2$ are straight chain alkyl groups containing from one to three carbons and $R^3$ is, alternatively, hydrogen or a straight chain alkyl group containing from one to three carbons. Preferably, $R^1$ and $R^2$ are methyl groups and $R^3$ is hydrogen or a methyl group. The stable formaldehyde/amine adduct is formed and stored in solution containing up to about 30 wt.% water based on the weight of the adduct and containing up to about 2 moles of a straight chain $C_{1\text{-}3}$ alkyl alcohol per mole of formaldehyde.

Preferably, the water content is up to 10 wt.%, more preferably less than about 2 wt.%, and most preferably as close to zero as possible. Absolute absence of water, while the most preferred, is not practical since minor amounts of water from the humidity in the atmosphere will always be present.

The amount of alcohol preferred increases as the amount of water present increases. That is, when water is essentially absent, no methanol need be added. At higher amounts of water, up to 2 moles per mole of formaldehyde is preferred. While higher amounts of alcohol are not detrimental to the stability of the adduct, there is an economic penalty associated with adding more than is needed. Within the preferred range of water concentration, the preferred alcohol concentration is 1 to 1.5 moles per mole of formaldehyde.

By "stable", it is meant that the adduct can be shipped to a user's site and stored for an extended period of time at room temperature or below without losing its effectiveness as a dewatering agent when it is reacted with a water-soluble polymer. Storage of three to four months or longer at temperatures of 30° C. or below are possible. Storage temperatures as low as 0° C. may be employed.

Use

The stable formaldehyde/amine adduct can be added to a solution of a water-soluble polymer such as polyacrylamide in one step to form a Mannich modified polymer which is effective alone or in its quaternized form in dewatering sludges. The Mannich modified compound that results has the following form:

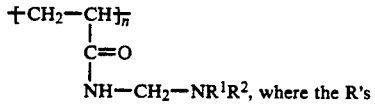

are as defined above and n is any number that results in a satisfactory molecular weight.

The water-soluble polymer may be any polymer known in the art for dewatering sludge. In particular, water-soluble vinyl addition polymers containing a majority of amide functional groups are useful. Polymers which fall into this category include polyacrylamide, polymethacrylamide, and various water-soluble copolymers of acrylamide and methacrylamide with monomers such as acrylic acid, methacrylic acid, and dimethylaminoethylmethacrylate. The preferred polymers are the polyacrylamides. The molecular weight of these polymers can range from several thousand to many million. Preferably the range is from about 200,000 to about 15 or 20 million.

The polymer may be in a water solution or in a water-in-oil emulsion. The polymers preferably are dispersed in water to form a stable dispersion without the use of surfactants. The preferred weight percent polymer is 1 to 10% in water and up to 50% in water-in-oil emulsions.

The temperature and pressure of reaction are not critical. Preferably the reaction is run at a temperature of 20° to 80° C. and atmospheric pressure. The time of reaction is not critical but may be completed in 96 hours at 20° C. or one hour at 50° C.

Process

The processes for making a stable formaldehyde/amine adduct of this invention in general comprise intimately contacting an amine with formaldehyde, preferably in the presence of the formaldehyde/amine adduct and, optionally, water and/or alcohol. The order of addition is not critical. Both reactants may be added simultaneously. The process may be continuous or batch. The process may be performed in a single step or in two steps.

The amines to be used in this invention are straight-chained secondary alkyl amines, the alkyl groups having from 1 to 3 carbon atoms. The preferred secondary amine is dimethylamine. They can be present as a mixture of amines. The amine can be present in aqueous, alcoholic or anhydrous form (50-100 wt.% amine). The preferred amine is anhydrous dimethylamine, but when used, temperature and pressure control are more difficult.

The formaldehyde to be used in this invention can be present in an aqueous solution (50-60 wt.% formaldehyde) or as paraformaldehyde. Preferably, paraformaldehyde of greater than 90% purity is used. The paraformaldehyde is added as slurry in water, $C_{1-3}$ alkyl alcohol or the adduct itself.

In either the one-step or the two-step process, the final adduct containing up to 30 wt.% water, preferrably up to 10 wt.% water, more preferrably less than 2 wt.% water and, particularly if more than a negligible amount of water is present, up to about 2 moles of a $C_{1-3}$ alkyl alcohol per mole of formaldehyde is produced.

The final product is separated from the reaction mixture by standard techniques and is isolated. The adduct formed should be cooled to 20° to 30° C. soon after manufacture, preferably within 1 to 2 hours, to prolong stability. Higher temperatures or longer storage can be tolerated particularly if water content is low and/or an alcohol is added.

One-Step Process for Making Formaldehyde/Amine Adduct from Dialkylamine and Formaldehyde or Paraformaldehyde The amine is brought into contact with the formaldehyde, preferably, at a high enough temperature to cause the amine and formaldehyde to react in a short time to produce the adduct. At higher temperatures, the time of reaction will be shorter than at lower temperatures. Higher temperatures will necessitate the use of higher pressure equipment to retain the higher vapor pressures. The temperature lower limit should be above the freezing point of the mixture, preferably above 0° C. Preferably, the temperature of reaction should be about 20° to 80° C., more preferably 20° to 50° C. and most preferably 20° to 35° C.

The amine can be added as a gas or liquid. When added as a gas, it preferably is bubbled into the formaldehyde solution or paraformaldehyde slurry.

The preferred mole ratio of formaldehyde to amine is 1:1.2 to 1:1, the more preferred ratio being 1:1.05. A slight excess of amine is desired to minimize the concentration of unreacted formaldehyde in the final product and the odor and toxicity problems associated therewith.

The product formed from this reaction of a secondary amine and formaldehyde is an alkanolamine as described in Walker in Formaldehyde, American Chemical Society Monograph Series, 3rd edition, pg. 360. It shows that the reaction between dimethylamine and formaldehyde results in an alkanolamine as shown below:

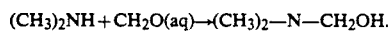

Applicant has found, however, that, when the reaction is carried out in the presence of an alcohol and particularly when paraformaldehyde in alcohol is reacted with anhydrous dimethylamine, the alkanolamine is at least partially converted to the alkoxy derivative as shown below:

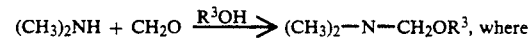

$R^3$ is a straight chain $C_{1-3}$ alkyl group.

Two-Step Process for Making Formaldehyde/Amine Adduct from Dialkylamine and Formaldehyde or Paraformaldehyde Applicant has also found that, when two moles of dialkylamine are first reacted with one mole of aqueous formaldehyde, alkylene bis(dialkylamine) is formed and can be easily removed from the water present. The alkylene bis(dialkylamine) can then be reacted with an additional mole of aqueous formaldehyde or, preferably with paraformaldehyde.

In the first step, from 2 to 3 moles, preferably 2 moles, of a secondary amine are reacted with one mole of formaldehyde to form the corresponding alkylene bis(dialkylamine). The alkylene bis(dialkylamine) will form an oil phase which is separated from the aqueous phase. Preferably about 10 to 50 wt.% aqueous sodium or potassium hydroxide is added to the aqueous phase to help separate the oil phase. Any excess amine will tend to stay with the aqueous phase and can be recycled to make more alkylene bis(dialkylamine).

In the second step, the alkylene bis(dialkylamine) is reacted with more formaldehyde. The preferred mole ratios are 0.9:1.1 to 1.1:0.9, the more preferred ratio being 1.05:1.0, of alkylene bis(alkylamine):aldehyde.

Temperature should be controlled in each step as in the one-step process. Preferably, the temperature of reaction in both steps should be about to 80° C., more preferably 20° to 50° C. and most preferably 20° to 35° C.

Without being tied down to a mechanism, it is believed that the dialkyaminoalkanol, or alkoxy derivative is formed as shown below:

STEP ONE:

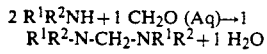

STEP TWO:

STEP TWO IN PRESENCE OF ALCOHOL:

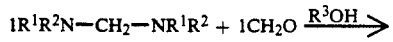

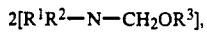

where $R^3$ is a straight chain $C_{1-3}$ alkyl group.

Because most of the water is removed in step one, the final product, even when aqueous formaldehyde is used in the second step, will have a lower water content and hence greater stability than when the one step process is used with the same two starting materials. When paraformaldehyde is added directly or in a non-water carrier such as a $C_{1-3}$ alkyl alcohol or the adduct itself in step two, the resulting product is predominantly $R^1R^2\text{-}N\text{-}CH_2OR^3$, where the $R^1$, $R^2$ and $R^3$ are as defined above, with essentially no water.

EXAMPLES

The following examples are given to further illustrate the invention and does not limit the scope of the invention. Unless otherwise indicated, all percentages are by weight.

Synthesis Examples

Formaldehyde/dimethylamine adducts can be prepared in a number of ways. The adducts tested for stability below were prepared by the following examples:

Example A

To 394 grams (3.5 moles) 40% aqueous dimethylamine in a one liter round bottom flask fitted with a thermometer, paddle stirrer and a cooling bath was added 173.5 grams (3.4 moles) 58.8% aqueous formaldehyde at a temperature of 20°-35° C. The product formed contained 54.3% water and was labeled Product "A".

Example B

To 717 grams (13.8 moles) 57.7% aqueous formaldehyde at 60° C. in a five liter round bottom flask fitted with a thermometer, paddle stirrer and a cooling bath was added 646.5 grams (13.3 moles) anhydrous dimethylamine thru a sparging tube at a temperature of 50°-60° C. The product formed was cooled to 23° C., contained 22.2% water and was labeled Product "B".

Example C

To 200 grams (1.96 moles) bis(dimethylamino)methane in a one liter round bottom flask fitted with a thermometer, paddle stirrer and a cooling bath was added 158 grams (1.95 moles 37% aqueous formaldehyde at a temperature of 15°-25° C. The product formed contained 17.9% water and was labeled Product "C".

Example D

To 30 grams (0.95 moles) paraformaldehyde suspended in 50 grams (1.56 moles) methanol in a 250 ml round bottom flask fitted with a stirrer, thermometer and cooling bath was added 49 grams (1.12 moles) anhydrous dimethylamine thru a sparging tube at a temperature of 30°-48° C. The product formed was cooled to 23° C., contained less than 1.0% water and was labeled Product "D".

Example E

To 642 grams (20.3 moles) powdered paraformaldehyde slurried in 480 grams (15.0 moles) methanol in a five liter round bottom flask fitted with a thermometer, paddle stirrer and cooling bath was added 962 grams (21.4 moles) anhydrous dimethylamine thru a sparging tube over a period of one hour at a temperature of 35°-50° C. The product formed was cooled to 23° C., contained less than 1.5% water and was labeled Product "E".

Example F

To 1086 grams (20.3 moles) 56.2% aqueous formaldehyde in a five liter round bottom flask fitted with a thermometer, paddle stirrer and cooling bath was added 963.6 grams (21.4 moles) anhydrous dimethylamine thru a sparging tube over a period of 40 minutes at a temperature of 50°-65° C. The product formed was cooled to 23° C., contained 24.3% water and was labeled Product "F".

Example G

To 545.8 grams (10.2 moles) 56.2% aqueous formaldehyde in a five liter round bottom flask fitted with a thermometer, paddle stirrer and cooling bath was added 311 grams (6.91 moles) anhydrous dimethylamine thru a sparging tube over a period of 40 minutes at a temperature of 50°-75° C. To this mixture was added 321.4 grams (10.18 moles) paraformaldehyde. Then, to the resulting slurry was added 653.4 grams (14.52 moles) anhydrous dimethylamine over a period of 40 minutes at a temperature of 50°-60° C. The product formed was cooled to 23° C., contained 13.9% water and was labeled Product "G".

Example H

To 392.6 grams of Product "F" was added 92 grams of water. The resulting product contained 37.8% water and was labled Product "H".

Example I

To 150 grams of Product "F" that had been stored for 27 days at 23° C. was added 20 grams of methanol. The resulting product, containing 11.8% methanol and 20.4% water, was labled Product "I".

Example J

To 150 grams of Product "G" that had been stored for 27 days at 23° C. was added 20 grams of methanol The resulting product, containing 11.8% methanol and 12.3% water, was labled Product "J".

Storage Stability Examples

The storage stability of the formaldehyde-dimethylamine adduct was measured by three methods: (1) formaldehyde content, (2) basicity as dimethylamine and (3) charge density measurements of the Mannich addition product of the formaldehyde-dimethylamine adduct to a water solution of five million molecular weight polyacrylamide. The following exemplify the critical parameters of water content and storage temperature.

Example 1

The formaldehyde/amine adducts of Examples A and C were stored at 2° and 23° for 14 and 17 months, respectively. Product "B" was stored for 2 months at 23° C. and for 5 weeks at 23° C. followed by an additional 3 weeks at 50° C. Product "D" was stored for 1 month at 23° C. and at 40' C. The following table summarizes the formaldehyde and dimethylamine loss for these samples.

| Product | Formaldehyde % Loss | Dimethylamine % Loss |
|---|---|---|
| Product "A" (54.3% water) | | |
| 14 Months @ 2° C. | 46.1 | 21.1 |
| 14 months @ 23° C. | 83.9 | 49.5 |
| Product "C" (17.9% water) | | |
| 17 Months @ 2° C. | 11.8 | 3.5 |
| 17 Months @ 23° C. | 72.9 | 43.3 |
| Product "B" (22.2% water) | | |
| 2 Months @ 23° C. | 13.6 | 3.9 |
| 5 Weeks @ 23° C. followed by 3 Weeks @ 50° C. | 65.1 | 31.6 |
| Product "D" (less than 1.0% water) | | |
| 1 Month @ 23° C. | 1.1 | −0.2 |
| 1 Month @ 40° C. | 2.7 | 1.2 |

Example 2

The formaldehyde-dimethylamine adduct of Examples A, B, C and D were used to prepare the cationically modified 5 million molecular weight (5 MM M.W.) polyacrylamide (PAM) as follows: To 100 grams (0.0282 equivalents) 2% water solution of 5 MM M.W. PAM in a 4 oz bottle was added 0.0141 equivalents of the formaldehyde-dimethylamine adduct, mixed and allowed to stand for six days. The cationic charge density was measured by titrating an aliquot of the polymer solution, adjusted to pH 2.5 with a standard solution of anionic polyvinylsulfuric acid-potassium salt with Toluidine Blue indicator.

| Product | Cationic Charge Density (meq +/gm active polymer) |
|---|---|
| Product "A" (54.3% water) | |
| 15 Months @ 2° C. | 1.7 |
| 15 months @ 23° C. | 0.7 |
| Product "C" (17.9% water) | |
| 18 Months @ 2° C. | 3.6 |
| 18 Months @ 23° C. | 1.7 |
| Product "B" (22.2% water) | 3.2 |
| 3 Months @ 23° C. | |
| Product "D" (less than 1.0% water) | |
| 2 Months @ 23° C. | 3.7 |
| 2 Months @ 40° C. | 3.4 |

Example 3

The formaldehyde-dimethylamine adduct of Examples E, F, G and H were used to prepare the cationically modified PAM and the charge densities of the resulting polymers were measured according to the procedure of Example 2. The results are in the following table.

| | Cationic Charge Density (meq +/gm active polymer) | | | |
|---|---|---|---|---|
| | | | 30 days @ 23° C. + | |
| Product | 20 days @ 23° C. | 53 days @ 23° C. | 18 days @ 20° C. | 18 days @ 40° C. |
| Product "E" (less than 1.5% water) | 3.8 | 3.9 | 3.9 | 3.7 |
| Product "F" (24.3% water) | 3.8 | 3.6 | 3.8 | 1.6 |
| | 3.7 | 3.7 | — | 1.7 |
| Product "G" (13.9% water) | 3.7 | 3.7 | 3.8 | — |
| Product "H" (37.8% water) | 3.4 | 3.1 | — | 1.4 |

Example 4

The formaldehyde-dimethylamine adduct of Examples E, I, and J were used to prepare the cationically modified PAM and the charge densities of the resulting polymers were measured according to the procedure of Example 2. The results are in the following table.

| | | Cationic Charge Density (meq +/gm active polymer) | |
|---|---|---|---|
| | Weight Ratio | 30 days @ 23° C. + 18 days @ | |
| Product | Water:Methanol | @ 23° C. | @ 40° C. |
| Product "E" (less than 1.5% water) | 1:15 | 3.9 | 3.7 |
| Product "I" (20.4% water) | 2:1 | 3.4 | 2.6 |
| | 2:1 | 3.5 | 2.8 |
| Product "J" (12.3% water) | 1:1 | 3.6 | 2.9 |

Example 5

The percent DMA loss in the following table were determined by titrating small samples of the adduct. Accordingly, the data presented may range from about 1% more to 1% less, that is for example, the loss for Product "E" after 75 days could be 0.3 to 2.3%. Storage temperature in each case was controlled at 23° C. for the days indicated.

| | | DMA Loss (Wt. %) after | | | |
|---|---|---|---|---|---|
| Product | % Water | 19 Days | 28 Days | 42 Days | 75 Days |
| "E" | less than 1.5 | 0 | 0 | −0.2 | 1.3 |
| "G" | 12.3 | 1.3 | 1.5 | 4.0 | 3.6 |
| "F" | 23.2 | 1.3 | 3.6 | 7.2 | 8.1 |
| "F" | 23.2 | 1.9 | 3.6 | 4.9 | 7.2 |
| "H" | 37.8 | 6.3 | 8.7 | 11.3 | 16.6 |

I claim:

1. A process for making a stable formaldehyde/secondary amine adduct comprising intimately contacting, in the presence of up to about 2 moles of a $C_{1-3}$ alkyl alcohol per mole of formaldehyde, 1 to 1.2 moles of a straight chain alkyl secondary amine, the alkyl groups having from 1 to 3 carbon atoms, with a mole of formaldehyde at a high enough temperature to cause the amine and formaldehyde to react in a short time to produce the adduct, the amine and the formaldehyde both being present in a sufficiently low concentration of water to produce the adduct containing no more than 30 wt.% water.

2. The process of claim 1 wherein the mole ratio of formaldehyde to amine is about 1:1.05.

3. The process of claim 1 wherein the formaldehyde is present as an aqueous solution containing 50 to 60 wt.% formaldehyde or as paraformaldehyde and the amine is present as an aqueous or alcoholic solution or in anhydrous form having a concentration of 50 to 100 wt.% amine.

4. The process of claim 1 wherein the alcohol is methyl alcohol.

5. A two-step process for making a stable formaldehyde/secondary amine adduct comprising:
   a. intimately contacting 2 to 3 moles of a straight chain secondary amine having from 1 to 3 carbon atoms with a mole of formaldehyde to produce a corresponding alkylene bis(dialkylamine) in an oil phase which is separated from an aqueous phase and then
   b. intimately contacting the corresponding alkylene bis(dialkylamine) with additional formaldehyde in a mole ratio of from 0.9:1.1 to 1.1:0.9 of alkylene bis(dialkylamine):formaldehyde to produce the adduct containing up to 30 wt.% water.

6. The process of claim 5 wherein about 10 to 50 wt.% aqueous sodium or potassium hydroxide is added to the aqueous phase in step (a).

7. The process of claim 6 wherein step (b) is in the presence of up to about 2 moles of a $C_{1-3}$ alkyl alcohol per mole of formaldehyde.

8. The process of claim 7 wherein the alcohol is methyl alcohol.

9. The process of claim 5 wherein the mole ratio of alkylene bis(alkylamine):aldehyde is about 1.05:1.0.

10. The process of claim 1 wherein the adduct formed is cooled to 20° to 30° C. soon after manufacture.

11. The process of claim 5 wherein the adduct formed is cooled to 20° to 30° C. soon after manufacture.

* * * * *